(12) United States Patent
Huh et al.

(10) Patent No.: US 12,108,826 B2
(45) Date of Patent: Oct. 8, 2024

(54) FACIAL PROTECTION APPARATUS

(71) Applicant: OTOS WING.CO., LTD., Seoul (KR)

(72) Inventors: Moon Young Huh, Seoul (KR); Sung Won Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 144 days.

(21) Appl. No.: 17/727,164

(22) Filed: Apr. 22, 2022

(65) Prior Publication Data
US 2022/0338591 A1    Oct. 27, 2022

(30) Foreign Application Priority Data

Apr. 23, 2021    (KR) .......................... 10-2021-0053110

(51) Int. Cl.
*A42B 3/20* (2006.01)

(52) U.S. Cl.
CPC ..................................... *A42B 3/20* (2013.01)

(58) Field of Classification Search
CPC .... A42B 3/18; A42B 3/20; A42B 3/22; A42B 3/221; A42B 3/225; A61F 9/06; A61F 9/067; A61F 9/068; A62B 17/04; A62B 18/04; A62B 18/045
See application file for complete search history.

(56) References Cited

U.S. PATENT DOCUMENTS

| | | | | |
|---|---|---|---|---|
| 6,102,033 A * | 8/2000 | Baribeau | ................ | A42B 3/225 2/427 |
| 7,003,802 B2 * | 2/2006 | Broersma | .............. | A63B 71/10 2/427 |
| 7,320,144 B2 * | 1/2008 | Katz | ....................... | A42B 3/185 2/9 |
| 7,681,257 B1 * | 3/2010 | Broersma | ................ | A42B 3/20 2/431 |
| 8,056,152 B2 * | 11/2011 | Brace | ..................... | A42B 3/225 2/424 |
| 8,166,578 B2 * | 5/2012 | Tan | ......................... | A61F 9/029 2/427 |

(Continued)

FOREIGN PATENT DOCUMENTS

| | | |
|---|---|---|
| EP | 0526919 A1 | 2/1993 |
| KR | 10-2001-0041780 A | 5/2001 |

(Continued)

OTHER PUBLICATIONS

Application No. DE10-2022-203902.5, Office Action mailed on Feb. 9, 2023, 8 pages.

(Continued)

*Primary Examiner* — F Griffin Hall
(74) *Attorney, Agent, or Firm* — Kilpatrick Townsend & Stockton LLP

(57) ABSTRACT

Provided is a facial protection apparatus including a main body having an opening area that is opened forward and being wearable by a user, a shield portion covering the opening area formed in the main body and detachably connected to the main body, and an opening/closing portion installed on the main body and opening/closing an insertion path of the shield portion that is inserted in the main body, so as to protect the face of the user against foreign matters during an operation and to have an improved convenience in use.

6 Claims, 8 Drawing Sheets

(56) References Cited

U.S. PATENT DOCUMENTS

| | | | | |
|---|---|---|---|---|
| 8,381,312 | B2* | 2/2013 | Seo | A61F 9/064 2/8.4 |
| 9,814,622 | B2* | 11/2017 | Sommers | A61F 9/06 |
| 10,226,383 | B2* | 3/2019 | Ambring | A41D 13/0518 |
| 10,757,995 | B2* | 9/2020 | Jacobsen | A42B 3/063 |
| 11,033,433 | B2* | 6/2021 | Sommers | A42B 3/225 |
| 11,278,077 | B2* | 3/2022 | Muske | A42B 3/28 |
| 11,324,274 | B2* | 5/2022 | Nilsson | A42B 3/225 |
| 11,376,161 | B2* | 7/2022 | Huh | A42B 3/225 |
| 11,759,364 | B2* | 9/2023 | Huh | A61F 9/06 2/8.3 |
| 11,786,406 | B2* | 10/2023 | Huh | B23K 9/322 2/8.5 |
| 2016/0183623 | A1* | 6/2016 | Didier | A42B 3/222 2/424 |
| 2022/0030977 | A1* | 2/2022 | Huh | A42B 1/247 |
| 2023/0120007 | A1* | 4/2023 | Green | A41D 13/1184 2/9 |

FOREIGN PATENT DOCUMENTS

| | | | |
|---|---|---|---|
| KR | 200333597 | Y1 | 11/2003 |
| KR | 200405938 | Y1 | 1/2006 |

OTHER PUBLICATIONS

Welding Accessories, ESAB Online Catalog; Archived in http://www.archive.org on May 14, 2011 at https://web.archive.org/web/20110514233831 /http://products.esab.com/Templates/T085.asp?id=55551, accessed on Feb. 6, 2023, 3 pages.

Helmets, Masks & Screens, Product Catalog—ESAB Welding & Cutting GmbH, Langenfeld Branch, Winkelsweg 178-180, D-40764 Langenfeld, Jan. 16, 2016, 3 pages.

Application No. KR 10-2021-0053110, Office Action mailed on Aug. 8, 2022, 4 pages.

Application No. KR 10-2021-0053110, Notice of Allowance mailed on Feb. 21, 2023, 6 pages.

* cited by examiner

FACIAL PROTECTION APPARATUS

CROSS-REFERENCE TO RELATED APPLICATION

This application is based on and claims priority under 35 U.S.C. § 119 to Korean Patent Application No. 10-2021-0053110, filed on Apr. 23, 2021, in the Korean Intellectual Property Office, the disclosure of which is incorporated by reference herein in its entirety.

BACKGROUND

1. Field

One or more embodiments of the disclosure relate to a facial protection apparatus.

2. Description of the Related Art

A worker generally wears a facial protection apparatus for protecting himself/herself against hazardous materials existing in an external environment during a disinfecting operation, or against light or high-temperature generated during a welding process such as an arc welding.

A facial protection apparatus may have various shapes and structures, for example, a shape covering eyes of a worker and vicinity of the eyes, a shape covering the head of the worker, etc.

According to the related art, a face shield arranged at a region corresponding to the eyes of a user may be damaged due to collision with foreign matters, and there may be a structural difficulty in releasing the face shield installed on a main body.

Also, a portion covering the head of the worker is integrally formed with the main body and is not replaceable, and thus, sweats of the worker, dust, hazardous materials in a work field may remain in a facial protection apparatus, and may cause inconvenience of the worker.

SUMMARY

Provided is a facial protection apparatus capable of protecting the face of a user against external foreign matters and improving convenience in use during an operation.

However, the above technical features are exemplary, and the scope of the disclosure is not limited thereto.

Additional aspects will be set forth in part in the description which follows and, in part, will be apparent from the description, or may be learned by practice of the presented embodiments of the disclosure.

According to an embodiment of the present disclosure, a facial protection apparatus includes: a main body having an opening area that is opened forward and being wearable by a user; a shield portion covering the opening area formed in the main body and detachably connected to the main body; and an opening/closing portion installed on the main body and opening/closing an insertion path of the shield portion that is inserted in the main body.

According to an embodiment of the present disclosure, the shield portion may be formed to have a transparency that varies.

According to an embodiment of the present disclosure, the shield portion may include a light-shielding layer.

According to an embodiment of the present disclosure, the opening/closing portion may include a plurality of opening/closing portions that are arranged at opposite sides of the main body on the basis of a center portion of the main body.

According to an embodiment of the present disclosure, the facial protection apparatus may further include a cover portion connected to the main body to surround head of the user.

According to an embodiment of the present disclosure, the cover portion may include: a cover frame portion connected to the main body; and a cover body connected to one end portion of the cover frame portion, the end portion being opposite to an end portion of the cover frame portion connected to the main body, and located on an outside of back of the head of the user.

Other aspects, features and advantages of the disclosure will become better understood through the accompanying drawings, the claims and the detailed description.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
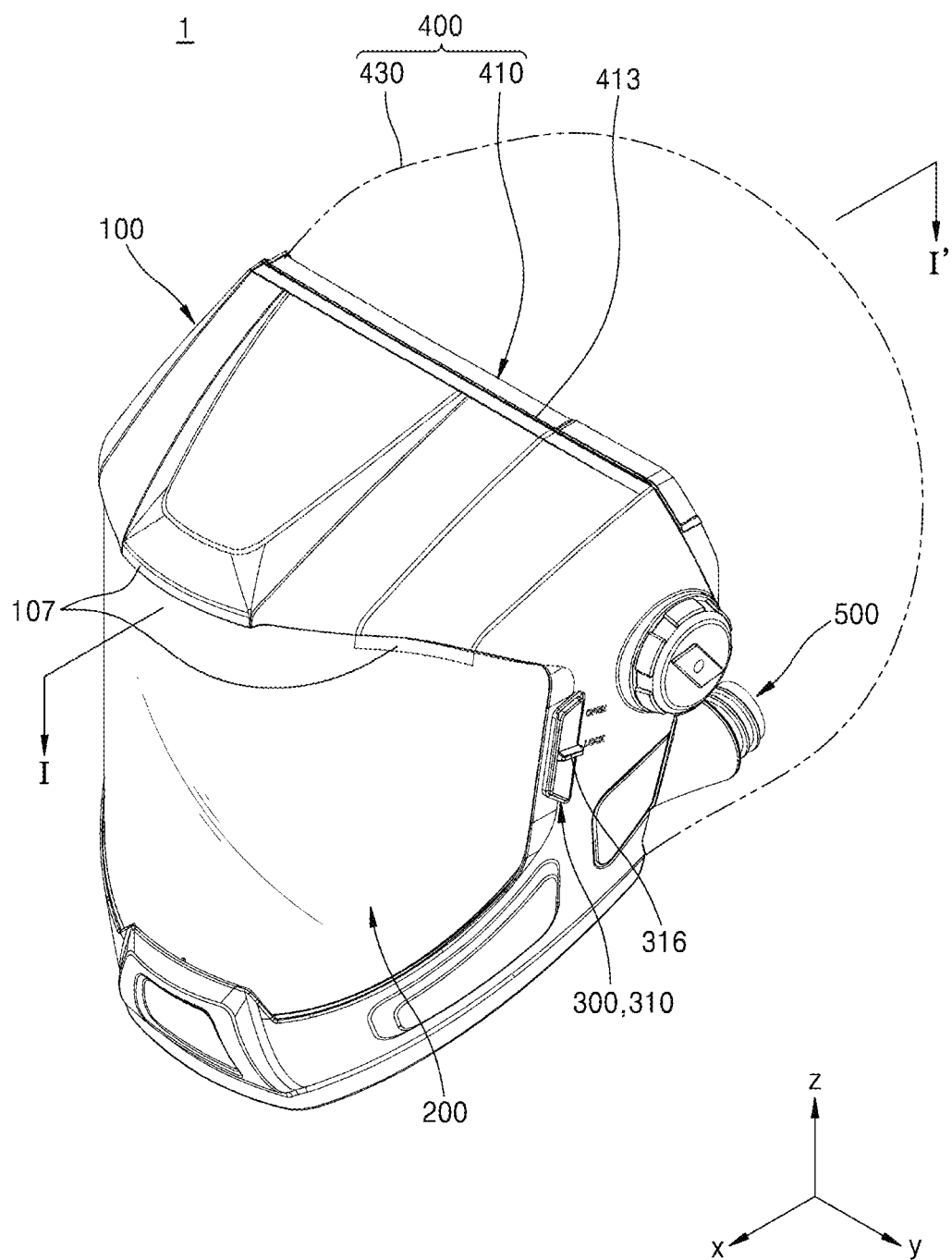
FIG. 1 is a perspective view of a facial protection apparatus according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Figure 2:
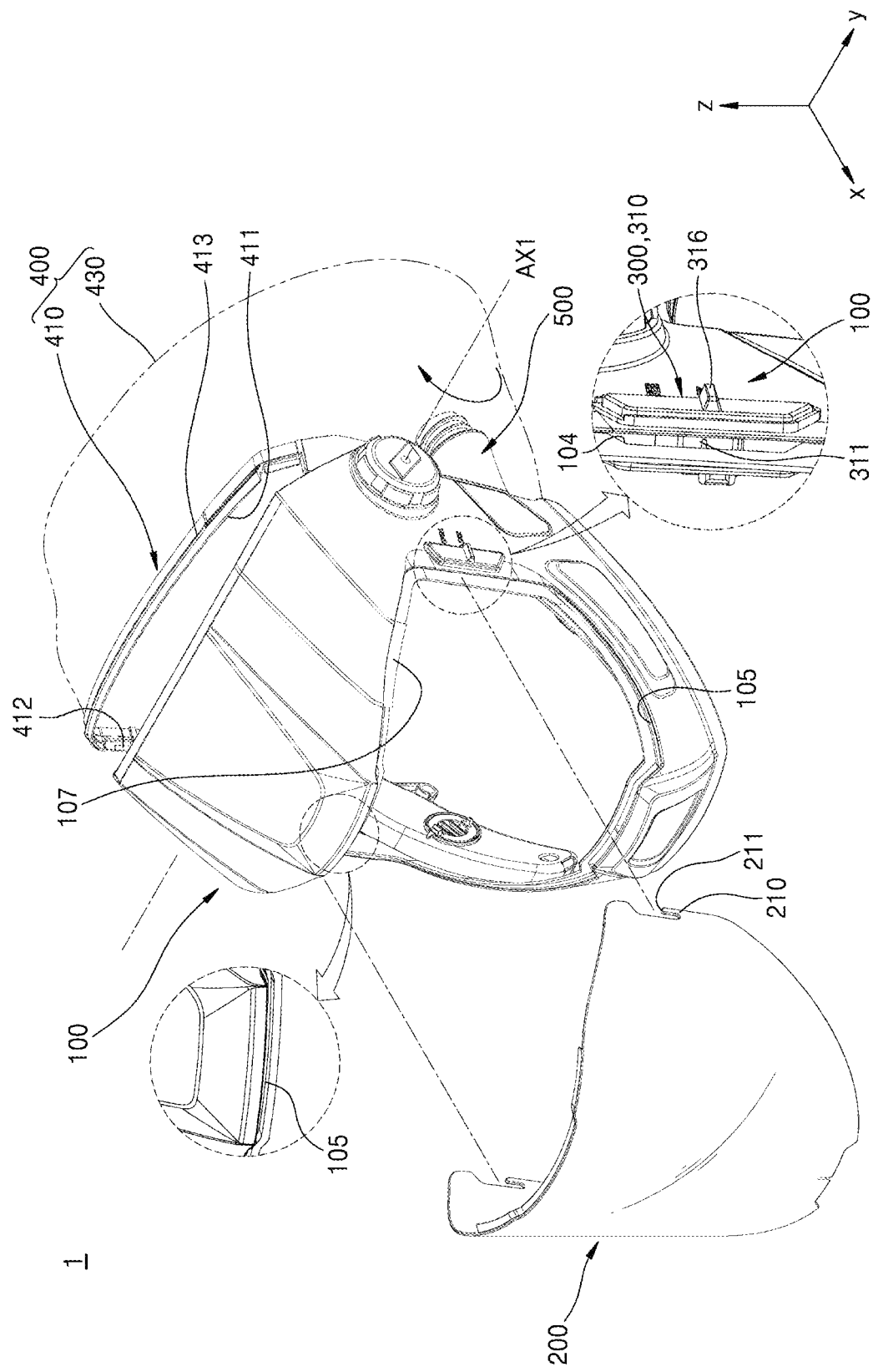
FIG. 2 is an exploded perspective view showing that a main body and a shield portion are disassembled, according to an embodiment of the present disclosure.
Figure 3:
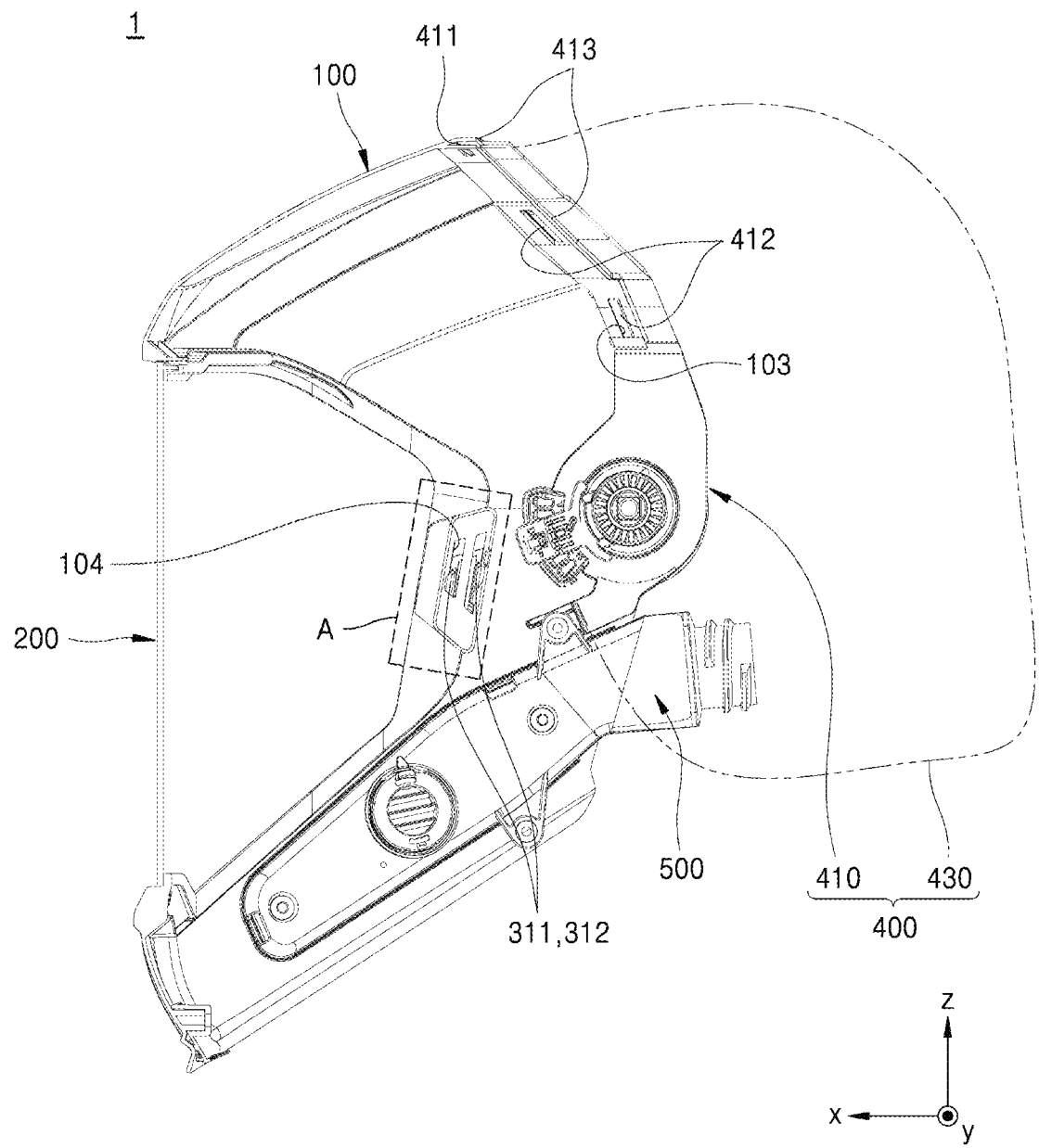
FIG. 3 is a diagram taken along line I-I' of FIG. 1.
Figure 4:
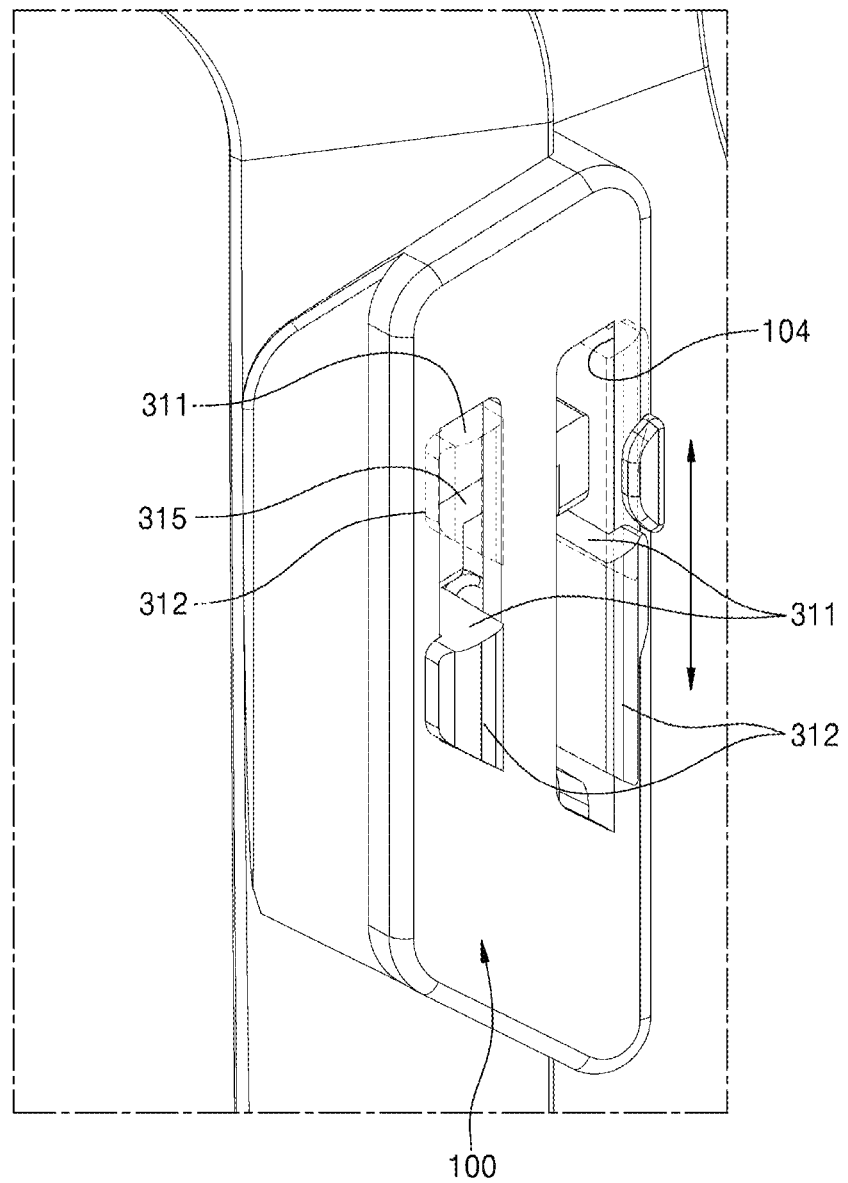
FIG. 4 is an enlarged view showing part A of FIG. 3.
Figure 5:
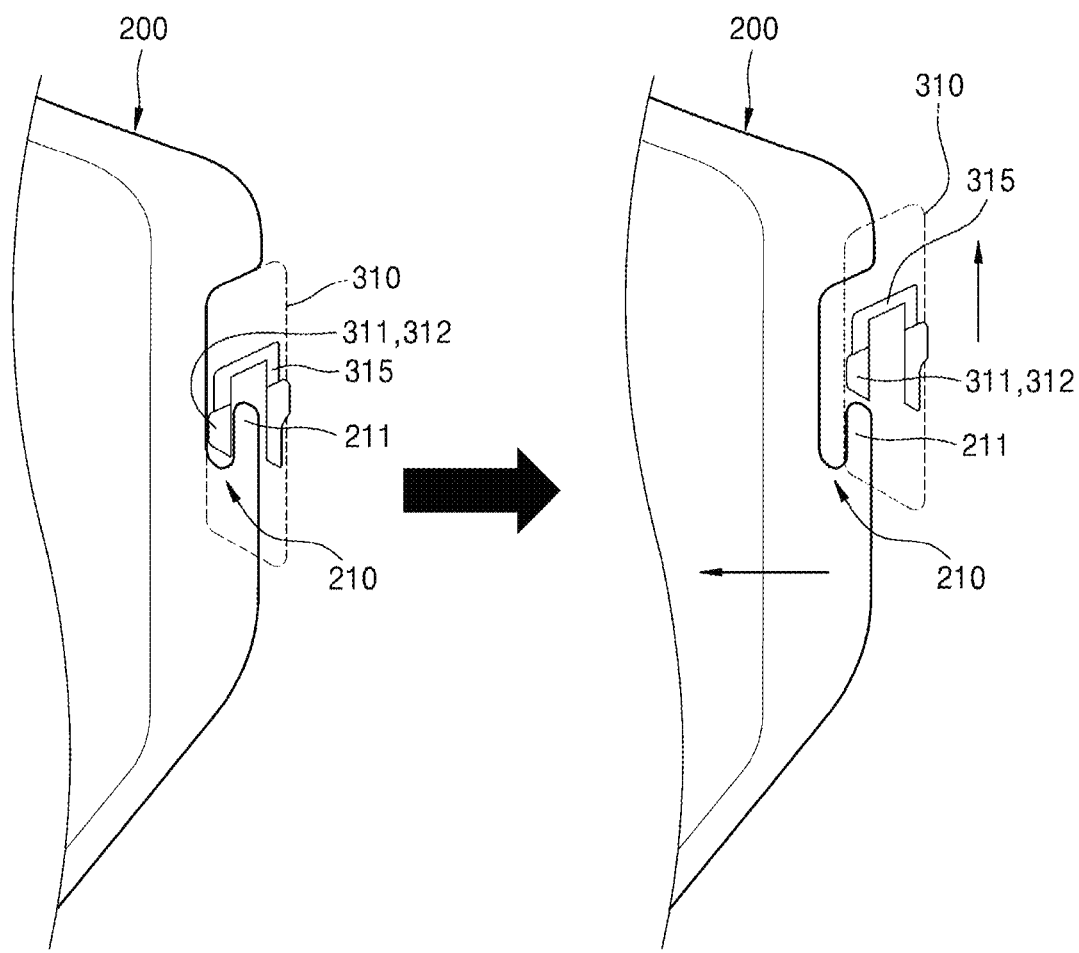
FIG. 5 is a diagram showing a state in which an opening/closing portion opens/closes a movement path of a shield portion.
Figure 6:
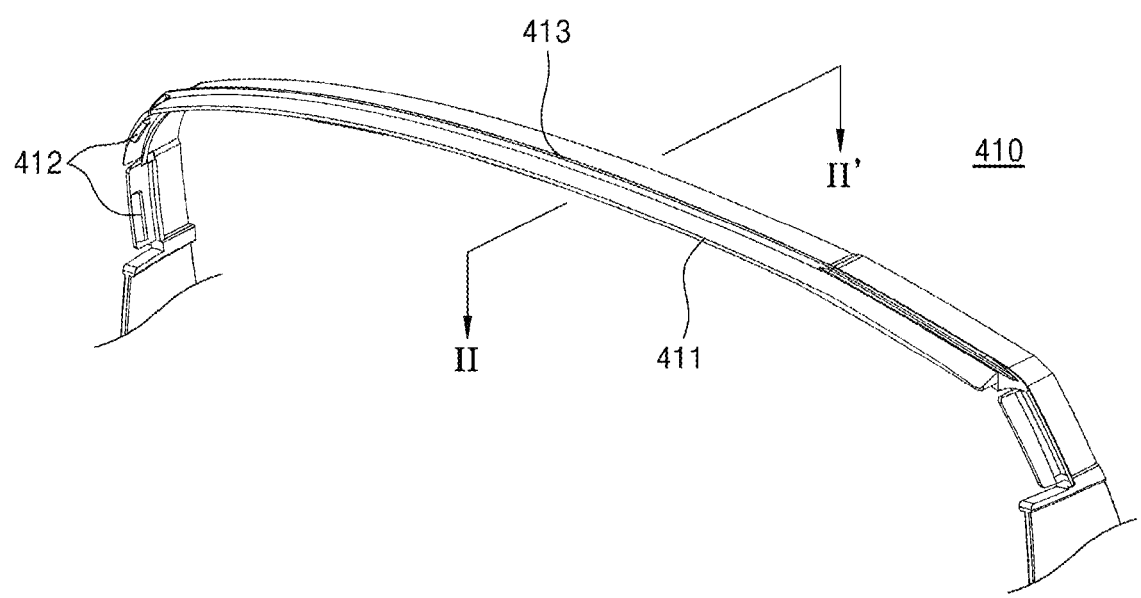
FIG. 6 is a partially perspective view of a cover portion according to an embodiment of the present disclosure.
Figure 7:
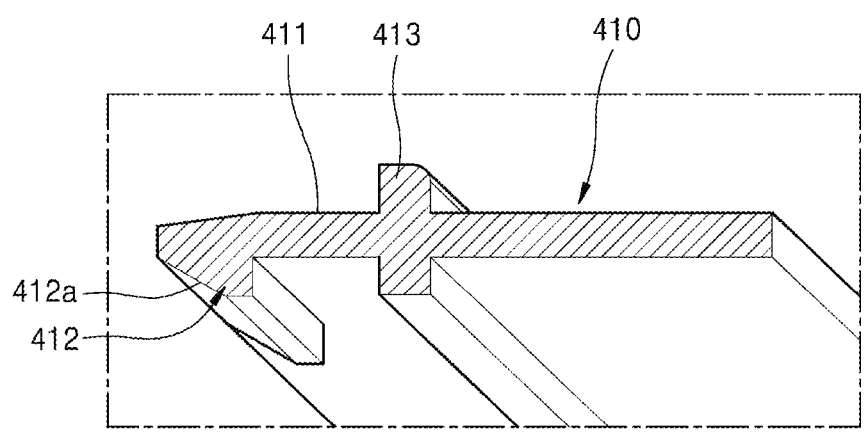
FIG. 7 is a diagram taken along line II-II' of FIG. 6.

FIG. 1 is a perspective view of a facial protection apparatus 1 according to an embodiment of the present disclosure. FIG. 2 is an exploded perspective view showing that a main body 100 and a shield portion 200 are disassembled, according to an embodiment of the present disclosure. FIG. 3 is a diagram taken along line I-I' of FIG. 1. FIG. 4 is an enlarged view showing part A of FIG. 3. FIG. 5 is a diagram showing a state in which an opening/closing portion 300 opens/closes a movement path of a shield portion. FIG. 6 is a partially perspective view of a cover portion 400 according to an embodiment of the present disclosure. FIG. 7 is a diagram taken along line II-II' of FIG. 6.

Referring to FIGS. 1 to 7, the facial protection apparatus 1 according to an embodiment of the present disclosure may include the main body 100, the shield portion 200, the opening/closing portion 300, the cover portion 400, and an injection portion 500.

Referring to FIGS. 1 to 4, the main body 100 according to the embodiment of the present disclosure has an opening area formed frontward (positive x-axis direction in FIG. 1), and may be provided to be wearable by a user.

Referring to FIGS. 1 and 2, the main body 100 according to the embodiment of the present disclosure has one surface facing the face of the user, and the opening area may be formed by opening an area of the surface, which is set in advance and faces the face of the user.

Referring to FIGS. 1 and 2, the opening area in one surface of the main body 100 may be covered by the shield portion 200 that will be described later.

Because the shield portion 200 according to the embodiment of the present disclosure covers the opening area of the main body 100, after the user wears the facial protection apparatus 1 according to the embodiment of the present disclosure and performs an operation such as a welding operation, a disinfecting operation, etc., there is an effect of blocking foreign matters, hazardous materials, etc. from being introduced from outside into an inner area of the facial protection apparatus 1, in which the face of the user is located.

Referring to FIG. 2, the main body 100 according to the embodiment of the present disclosure may include an insertion portion 105 that is formed as a groove portion having a certain depth along a circumference of the opening area that is formed on a front side (based on FIG. 2).

Referring to FIG. 2, the shield portion 200 may be inserted in the insertion portion 105 according to the embodiment of the present disclosure.

The shield portion 200 is inserted in the insertion portion 105 along the circumference according to the embodiment of the present disclosure, and an outer surface of the shield portion 200 inserted in the insertion portion 105 may come into close contact with an inner surface of the insertion portion 105.

As such, introduction of foreign matters, hazardous materials, etc. through a gap formed between the shield portion 200 and the main body 100 may be effectively blocked according to the embodiment of the present disclosure.

Referring to FIGS. 1 and 2, due to the insertion portion 105 according to the embodiment of the present disclosure, when the shield portion 200 covers the opening area formed in the main body 100, an insertion path of the shield portion 200 into the main body 100 may be stably guided to the user.

In an alternative embodiment, the shield portion 200 may be entirely inserted in the insertion portion 105 according to an embodiment of the present disclosure, and thus, the user may completely open the opening area formed in the main body 100 as necessary.

Referring to FIGS. 1 and 2, in the main body 100 according to the embodiment of the present disclosure, the insertion portion 105 is formed along the circumference of the front side facing the shield portion 200, and a cover insertion portion (not depicted by a reference numeral) may be formed as a groove portion having a certain depth along a circumference of a preset section in a rear side facing the front side (based on FIG. 2).

A cover frame 410, in particular, a cover frame body 411, that will be described later, may be inserted in the cover insertion portion according to an embodiment of the present disclosure.

Referring to FIG. 3, a seating portion 103 may be formed in one of the inner surfaces of the cover insertion portion according to the embodiment of the present disclosure, and a protrusion portion 412 that protrudes from the cover frame body 411 toward the main body 100 in which the seating portion 103 is formed, in particular, a surface of the cover insertion portion, may be inserted in the seating portion 103.

Referring to FIG. 3, the seating portion 103 formed in the main body 100 according to the embodiment of the present disclosure, in particular, the cover insertion portion, may pass through a surface of the main body 100.

As such, during a process of inserting the cover frame portion 410, in particular, the cover frame body 411 in the cover insertion portion, the protrusion portion 412 is seated while being placed on the seating portion 103, and after that, when the user wants to separate the cover frame portion 410, in particular, the cover frame body 411, from the main body 100, the user may push the protrusion portion 412 in the seating portion 103 upward from a side (lower side in FIG. 3) facing the other side (upper side in FIG. 3) of the seating portion 103 in which the protrusion portion 412 is inserted, so as to separate the cover frame portion 410, in particular, the cover frame body 411, from the cover insertion portion formed in the main body 100.

Referring to FIGS. 2, 3, and 4, a through-hole portion 104 may be formed in the main body 100 according to the embodiment of the present disclosure, so that a passing portion 311 formed on the opening/closing portion 300 that will be described later, in particular, an opening/closing body 310 may pass therethrough.

Referring to FIG. 4, the passing portion 311 formed on the opening/closing body 310 passes through the through-hole portion 104 formed in the main body 100 and comes into contact with the inner surface of the main body 100, and in particular, a hook portion 312 formed at one end of the passing portion 311 is hooked on the through-hole portion 104 and the passing portion 311 may be arranged on the main body 100.

Referring to FIG. 4, the opening/closing portion 300, in particular, the opening/closing body 310 on which the passing portion 311 is formed, may be movable on the main body 100 in a preset direction (vertical direction in FIG. 4).

When the opening/closing body 310 according to the embodiment of the present disclosure is moved in the preset direction (vertical direction in FIG. 4), a movement path of an engagement portion 210 of the shield portion 200 and a bent portion 211 that protrudes from the engagement portion 210 may be opened/closed, and when the movement path is opened, the user may release the connection of the shield portion 200 from the main body 100 and may remove the shield portion 200.

Referring to FIGS. 2 and 4, when the shield portion 200 is connected to the main body 100, while the opening/closing body 310 is moved in a first direction (a direction from the lower to upper side in FIG. 5), the movement path of the shield portion 200, in particular, the engagement portion 210 and the bent portion 211 formed on the engagement portion 210, is opened and the shield portion 200 may be inserted in the insertion portion 105 of the main body 100. Then, when the opening/closing body 310 is moved in a second direction (a direction from upper to lower side in FIG. 5), the movement path of the bent portion 211 formed on the engagement portion 210 is closed and the separation of the shield portion 200 from the main body 100 may be prevented.

Referring to FIG. 4, the inner surface of the main body 100 according to the embodiment of the present disclosure may be in contact with a stopper portion 315 formed on the opening/closing body 310, and the movement path of the opening/closing body 310 may be restricted by the stopper portion 315.

Referring to FIG. 4, according to the embodiment of the present disclosure, there may be a plurality of through-hole portions 104 so as to correspond to a plurality of passing portions 311 formed on the opening/closing body 310.

Referring to FIG. 2, the cover portion 400, in particular, the cover frame portion 410, may be rotatably connected to the main body 100 according to the embodiment of the present disclosure. In detail, the cover frame portion 410 may rotate in a clockwise direction or a counter-clockwise direction about a first axis AX1 as a rotating center axis.

The user may rotate the cover portion 400, in particular, the cover frame portion 410, relative to the main body 100 so as to extract the cover frame portion 410 from the cover insertion portion formed as a groove portion in the rear side of the main body 100 and the connection between the main body 100 and the cover frame portion 410 may be released.

Referring to FIGS. 1 and 2, the insertion portion 105 is formed along the circumference of the opening area formed in the main body 100, and a separation prevention portion 107 may protrude outward from a preset region on the opening area.

Referring to FIGS. 1 and 2, the separation prevention portion 107 may protrude toward the center of the opening area formed in the main body 100, and as such, the separation of the shield portion 200 from the insertion portion 105 may be prevented.

Referring to FIG. 1 and FIG. 2, a plurality of separation prevention portions 107 may be provided according to the embodiment of the present disclosure, and the separation prevention portions 107 may be spaced apart from one another at a plurality of points along the circumference of the opening area formed in the main body 100.

The separation prevention portion 107 according to the embodiment of the present disclosure may protrude toward the opening area along the inner circumference of the main body 100, in which the opening area is formed.

As such, after the shield portion 200 is inserted in the insertion portion 105 formed in the main body 100, the separation prevention portion 107 covers a certain region of the shield portion 200 and prevents the separation of the shield portion 200 from the main body 100.

Referring to FIGS. 1, 2, and 3, the injection portion 500 may be connected to the main body 100 according to the embodiment of the present disclosure.

The injection portion 500 may be connected to an external device, and may receive fresh air, oxygen, etc. from the external device and transfer the air, oxygen, etc. to the user in the main body 100.

Because the injection portion 500 according to the embodiment of the present disclosure transfers the air, oxygen, etc. to the inner space of the main body 100, an environment in which the user may smoothly breathe during an operation such as a welding operation, a disinfecting operation, etc. may be established and an operating efficiency may be improved.

Referring to FIGS. 1, 2, 3, and 5, the shield portion 200 according to the embodiment of the present disclosure covers the opening area formed in the main body 100, and may be detachably connected to the main body 100.

The shield portion 200 according to an embodiment of the present disclosure may have a transparency that varies. The user may secure a sight of the front part of the facial protection apparatus 1 through the shield portion 200.

The shield portion 200 according to the embodiment of the present disclosure may include a transparent material and may have a rigidity set in advance.

As such, the user wearing the facial protection apparatus 1 according to the embodiment of the present disclosure performs the operation while securing the front sight, and during this process, foreign matters generated outside may be prevented from approaching and colliding with the face of the user in an unexpected situation.

The shield portion 200 according to the embodiment of the present disclosure may include a light-shielding layer (not defined by a reference numeral).

The light-shielding layer may shield a light source introduced through the shield portion 200, protect eyesight of the user against the light source generated during the welding operation, and prevent the light source from interrupting with the operation.

The light-shielding layer according to the embodiment of the present disclosure may include a light-shielding film.

However, one or more embodiments are not limited thereto, various modifications may be possible within the technical scope of the disclosure, for example, coating the shield portion with a light-shielding solution, provided that the light source generated outside may be prevented from directly being incident to the user who wears the facial protection apparatus 1.

Referring to FIG. 2, the shield portion 200 according to the embodiment of the present disclosure may be inserted into the insertion portion 105 that is formed as a groove portion along the circumference of the opening area formed in the main body 100 toward the front portion.

Because the shield portion 200 according to the embodiment of the present disclosure is inserted in the insertion portion 105 that is formed to a preset depth along the circumference of the opening area in the main body 100 and the outer surface of the shield portion 200 is in close contact with the inner surface of the main body 100, in particular, the insertion portion 105, introduction of the external foreign matters into the space formed between the main body 100 and the shield portion 200 may be blocked.

Additionally, due to the insertion portion 105 having the certain depth along the circumference of the opening area formed in the main body 100 according to the embodiment of the present disclosure, the user may be stably provided with a connecting path between the shield portion 200 and the main body 100, and the shield portion 200 may be easily attached to/detached from the main body 100.

In addition, the user may easily connect or disconnect the shield portion 200 to/from the main body 100, and the shield portion 200 that is contaminated and damaged due to the foreign matters may be easily replaced.

Referring to FIGS. 2 and 5, the engagement portion 210 may protrude from one side of the shield portion 200. In detail, the engagement portion 210 may protrude outward from the side portion of the shield portion 200.

Referring to FIGS. 2 and 5, a plurality of engagement portions 210 may be provided and may be arranged at opposite sides of the shield portion 200. However, one or more embodiments are not limited thereto, and various modifications are possible, for example, a single engagement portion 210 may protrude from one side of the shield portion 200.

In the present specification, an example in which a pair of engagement portions 210 are provided on opposite sides of the shield portion 200 will be described.

Referring to FIGS. 2 and 5, the engagement portions 210 according to the embodiment of the present disclosure are arranged at opposite sides of the shield portion 200 based on a center portion of the shield portion 200, and the bent portion 211 may be formed on a preset section.

Referring to FIG. 5, the bent portion 211 according to the embodiment of the present disclosure protrudes from one side (right side in FIG. 5) of the shield portion 200 in the first direction (a direction from left to right in FIG. 5), and may be bent to extend in the second direction (a direction from lower to upper side in FIG. 5) at a preset section.

As such, the bent portion 211 may be spaced a certain distance from one side (a right side in FIG. 5) of the shield portion 200 from which the engagement portion 210 does not protrude. The opening/closing body 310, in particular, the passing portion 311 that will be described later may be arranged in the space between the bent portion 211 and one side of the shield portion 200.

Referring to FIG. 5, the passing portion 311 being located in the space formed between the bent portion 211 and one side of the shield portion 200 denotes that the passing portion 311 is located on an insertion or extraction path of the shield portion 200 to/from the main body 100.

As such, when the passing portion 311 formed on the opening/closing portion 300, in particular, the opening/closing body 310, is located in the space formed between the bent portion 211 and one side of the shield portion 200 while the shield portion 200 is inserted in the insertion portion 105 formed in the main body 100, the shield portion 200 may be stably fixed to the main body 100, and the separation of the shield portion 200 from the insertion portion 105 formed in the main body 100 may be prevented.

Additionally, due to at least one separation prevention portion 107 protruding from the preset section along the circumference of the opening area in the main body 100, the separation of the shield portion 200 inserted in the main body 100 toward the front side of the facial protection apparatus may be secondarily prevented.

Referring to FIG. 5, when the user moves the opening/closing portion 300, in particular, the opening/closing body 310, in a preset direction (a direction from lower to upper side in FIG. 5) on the main body 100, the passing portion 311 is separated from the space formed between the engagement portion 210 protruding from the shield portion 200, in particular, the bent portion 211, and one side of the shield portion 200 and the shield portion 200 is separated from the insertion portion 105 formed in the main body 100 to be disconnected from the main body 100.

Referring to FIGS. 2 to 5, as the user moves the opening/closing portion 300 according to the embodiment of the present disclosure in the direction set in advance (a vertical direction in FIG. 5), the position of the passing portion 311 formed on the opening/closing portion 300, in particular, the opening/closing body 310, on the insertion path of the shield portion 200 may be adjusted.

Referring to FIG. 4, the insertion or separation path of the shield portion 200 into/from the main body 100 may be opened/closed according to the position variation of the passing portion 311 according to the embodiment of the present disclosure, and the shield portion 200 may be easily attached to/detached from the main body 100.

In the present disclosure, the engagement portions 210 protrude outward from opposite sides of the shield portion 200, the bent portion 211 is formed by bending one end portion of the engagement portion 210 at the preset section, and the space may be formed between the bent portion 211 that is one end of the engagement portion 210 and the side portion of the shield portion 200.

However, one or more embodiments are not limited thereto, and various modifications are possible, for example, the passing portion 311 may be arranged after partially cutting the shield portion 200 within the technical idea of arranging the passing portion 311 on the movement path of the shield portion 200.

Referring to FIGS. 1 to 5, the opening/closing portion 300 according to the embodiment of the present disclosure is installed on the main body 100 and may open/close the insertion path of the shield portion 200 inserted in the main body 100.

The opening/closing portion 300 according to the embodiment of the present disclosure may include the opening/closing body 310. One side of the opening/closing body 310 is on the outside of the main body 100, and the opening/closing body 310 may be moved on the main body 100 in a preset direction.

Referring to FIGS. 1, 2, 4, and 5, the opening/closing body 310 according to the embodiment of the present disclosure may be moved in the vertical direction (based on FIG. 4). However, one or more embodiments are not limited thereto, and various modifications are possible within the technical idea of arranging the opening/closing body 310 on the insertion path of the shield portion 200 into the main body 100.

Referring to FIGS. 1 and 3, a plurality of opening/closing portions 300 may be provided according to the embodiment of the present disclosure, and the plurality of opening/closing portions 300 may be arranged respectively on opposite sides based on the center portion of the main body 100. In detail, FIG. 3 shows an inside of the main body 100 corresponding to a left side (based on FIG. 1), after being taken along line I-I' of FIG. 1.

Structures, operational principles, and effects of the opening/closing portions 300 on opposite sides of the main body 100 according to the embodiment of the present disclosure are the same as each other, and thus, the structure of the opening/closing portion 300 located on the left side (based on FIG. 1) on the basis of the center portion of the main body 100 will be described with reference to FIGS. 3 to 5.

Referring to FIGS. 1 to 5, the opening/closing portion 300 according to the embodiment of the present disclosure includes the opening/closing body 310, and the passing portion 311 may protrude from one surface of the opening/closing body 310, the surface facing the main body 100, in a direction toward the main body 100.

Referring to FIG. 4, the passing portion 311 protruding from the main body 100 according to the embodiment of the present disclosure may pass through the main body 100.

Referring to FIG. 4, the main body 100 according to the embodiment of the present disclosure may have the through-hole portion 104 that is formed as a through-hole by a preset section along the central axis in the lengthwise direction (a vertical direction in FIG. 4).

Referring to FIG. 4, because the through-hole portion 104 is formed in the main body 100, the passing portion 311 formed on the opening/closing body 310 may pass therethrough and the through-hole portion 104 may provide the movement path of the passing portion 311.

Referring to FIGS. 2 to 5, a plurality of passing portions 311 may be provided according to the embodiment of the present disclosure, and the plurality of passing portions 311 may be spaced apart from one another by a certain interval.

When the plurality of passing portions 311 are formed on the opening/closing body 310, the movement of the opening/closing body 310 on the main body 100 may be stably controlled as compared with a single passing portion 311, and the user may feel convenience in manipulating the opening/closing portion 300.

Referring to FIGS. 3 to 5, the hook portion 312 may protrude from, in a different extending direction, an outer end portion of the passing portion 311 that protrudes from the opening/closing body 310 according to the embodiment of the present disclosure.

Referring to FIG. 4, the hook portion 312 according to the embodiment of the present disclosure may extend outward at a certain angle with respect to the direction in which the passing portion 311 extends, and the hook portions 312 that are respectively formed on the outer end portions of the plurality of passing portions 311 may extend away from one another.

Referring to FIG. 4, the hook portion 312 according to the embodiment of the present disclosure may be placed on the through-hole portion 104 of the main body 100, and may be in surface-contact with the main body 100. Because the hook portion 312 according to the embodiment of the present disclosure is in surface-contact with the main body 100, the separation of the opening/closing body 310 from the main body 100 may be prevented and may be stably arranged on the main body 100.

Referring to FIG. 5, the passing portion 311 according to the embodiment of the present disclosure may be located on the movement path (a transverse direction in FIG. 5) of the bent portion 211 that is formed on the shield portion 200, in particular, on the engagement portion 210.

Referring to the left side of FIG. 5, the passing portion 311 is located on the movement path of the bent portion 211, the movement of the bent portion 211 protruding from the shield portion 200, in particular, the engagement portion 210, is prevented by the passing portion 311, and the installation state of the shield portion 200 in the main body 100 may be maintained.

Referring to the right side of FIG. 5, the passing portion 311 is spaced apart from the bent portion 211 protruding from the engagement portion 210, and the opening/closing body 310, in particular, the passing portion 311, is moved in the preset direction (a direction from lower to upper side in FIG. 5) due to an external force of the user, etc.

As such, the shield portion 200 may be separated from the main body 100, and after separating the shield portion 200 from the main body 100, operations such as cleaning, replacement, etc. may be performed.

Referring to FIGS. 4 and 5, the inner surface of the main body 100 according to the embodiment of the present disclosure may be in contact with the stopper portion 315 formed on the opening/closing body 310, and the movement path of the opening/closing body 310 may be restricted by the stopper portion 315.

Referring to FIGS. 1 and 2, a contact portion 316 may protrude upward from the opening/closing body 310 according to the embodiment of the present disclosure. In detail, the contact portion 316 may protrude outward from one surface of the opening/closing body 310, wherein the one surface is opposite to the other side from which the passing portion 311 protrudes while facing the main body 100.

Because the contact portion 316 protrudes from the outer surface of the opening/closing body 310 according to the embodiment of the present disclosure, a frictional force between the opening/closing body 310 and the hand of the user may increase so that the opening/closing body 310 may be easily moved on the main body 100 when the user touches the opening/closing body 310 by his/her hand in order to move the opening/closing body 310.

In other words, as compared with an example in which the opening/closing body 310 has a flat surface without forming the contact portion 316, the movement of the opening/closing body 310 may be precisely controlled due to the contact.

In the present disclosure, the passing portion 311 formed on the opening/closing body 310 is arranged on the movement path of the bent portion 211 formed on the shield portion 200, in particular, the engagement portion 210, and thus, the movement path of the bent portion 211 is opened/closed such that the shield portion 200 may be inserted in or detached from the main body 100.

However, one or more embodiments are not limited thereto, and various modifications are possible. For example, the shield portion 200 is rotatably connected to the opening/closing portion 300 after being inserted in the main body 100, and the user may rotate the shield portion 200, during the operation, in the clockwise direction or counter-clockwise direction about a rotating center shaft set in advance without completely separating the shield portion 200 from the main body 100, in order to open or close the opening area formed in the main body 100.

Referring to FIGS. 1 to 3, 6, and 7, the cover portion 400 according to the embodiment of the present disclosure is connected to the main body 100 so as to surround the head of the user, and may include the cover frame portion 410 and a cover body 430.

The cover frame portion 410 according to FIGS. 1 and 2 and the embodiment of the present disclosure is connected to the main body 100 and may be rotatably connected to the main body 100.

Referring to FIG. 2, opposite sides of the cover frame portion 410 according to the embodiment of the present disclosure are rotatably connected to opposite sides of the main body 100, and may be rotated in the clockwise direction or counter-clockwise direction about the first axis AX1 that is a rotating center shaft set in advance.

Referring to FIGS. 1, 2, and 3, one side (a front side in FIG. 2) of the cover frame portion 410 according to the embodiment of the present disclosure may be connected to the main body 100, and the cover body 430 that will be described later may be connected to the other side (a back side in FIG. 2) of the cover frame portion 410.

Referring to FIGS. 1 to 3, 6, and 7, the cover frame portion 410 according to the embodiment of the present disclosure may be connected to the main body 100 when a preset region of the cover frame portion 410 is inserted in the main body 100.

Referring to FIG. 6, the cover frame portion 410 may include the cover frame body 411, and the cover frame body 411 may be inserted in a cover insertion portion (not defined by a reference numeral) formed as a groove portion along the rear circumference of the main body 100.

The cover insertion portion may be formed as the groove portion along the circumference of the rear end portion (a right side in FIG. 3) of the main body 100 facing the cover portion 400, in particular, the cover frame portion 410.

When the cover insertion portion is inserted in the main body 100 according to the embodiment of the present disclosure and the cover frame portion 410, in particular, the cover frame body 411, is inserted in the cover insertion portion, the cover portion 400 may be inserted in and connected to the main body 100 along a path set in advance.

While the outer surface of the cover frame body 411 and the inner surface of the cover insertion portion formed in the main body 100 come into close contact with each other, introduction of foreign matters from outside into a space surrounded by the main body 100 and the cover portion 400 may be prevented.

Referring to FIGS. 6 and 7, the protrusion portion 412 may protrude outward from one surface (a lower surface in FIG. 7) of the cover frame portion 410, in particular, the cover frame body 411 according to the embodiment of the present disclosure.

Referring to FIG. 3, the seating portion 103 having a certain depth may be formed in the main body 100 so that the protrusion portion 412 of the cover frame body 411 may be inserted therein, according to the embodiment of the present disclosure.

A plurality of protrusion portions 412 may be provided on one surface of the cover frame body 411 according to the embodiment of the present disclosure, and the plurality of protrusion portions 412 may be spaced apart from one another. To correspond to the plurality of protrusion portions 412, a plurality of seating portions 103 may be formed in the main body 100 according to the embodiment of the present disclosure.

Referring to FIG. 3, the seating portion 103 according to the embodiment of the present disclosure may be formed in one surface of the main body 100, in particular, the surface facing one surface of the cover frame body 411 from which the protrusion portion 412 protrudes in the inner circumferential surface of the cover insertion portion, and may penetrate through the surface.

As such, when the user wants to disconnect the cover frame portion 410, in particular, the cover frame body 411, from the main body 100, the user may put his/her hand in the main body 100, in particular, the seating portion 103 formed through the cover insertion portion, and push the protrusion portion 412 in the seating portion 103 to release the coupling between the cover frame body 411 and the main body 100.

Referring to FIG. 7, the protrusion portion 412 protruding from the cover frame body 411 according to the embodiment of the present disclosure may have an inclined surface 412a.

Because the inclined surface 412a is formed on the protrusion portion 412, the cover frame portion 410, in particular, the cover frame body 411, may be easily inserted in the cover insertion portion formed in the main body 100.

Referring to FIGS. 1, 2, 3, 6, and 7, a step portion 413 may protrude outward from the cover frame portion 410 along the circumference according to the embodiment of the present disclosure.

Because the step portion 413 extends from the cover frame portion 410, when a preset portion of the cover frame portion 410, in particular, the cover frame body 411, is inserted in the cover insertion portion formed in the main body 100, the step portion 413 protruding from the cover frame portion 410 comes into contact with the main body 100 and controls the inserted portion of the cover frame body 411.

Referring to FIGS. 1, 2, and 3, the cover body 430 according to the embodiment of the present disclosure is connected one end portion of the cover frame portion 410, which is opposite to the other end portion of the cover frame portion 410 connected to the main body 100, and may be located on an outside of back of the head of the user.

The cover body 430 according to the embodiment of the present disclosure may include a cotton material, and the user may put his/her head into the cover body 430 to wear the facial protection apparatus 1.

Although not shown in the drawings, a length adjusting portion (not shown) for adjusting length may be installed on a preset region of the cover body 430, except for the region connected to the cover frame portion 410.

The length adjusting portion may include an elastically deformable material. The user may put his/her head into the cover body 430 after stretching the length adjusting unit, and then, the region of the cover body 430 where the length adjusting portion is installed comes into contact with the body of the user due to an elastic recovery force to prevent contact with the hazardous materials and foreign matters existing outside.

The cover body 430 according to the embodiment of the present disclosure may be connected to the cover frame portion 410 in various ways, e.g., adhering, sticking, etc.

Referring to FIGS. 1 to 3, the injection portion 500 according to the embodiment of the present disclosure is connected to the main body 100 and may be connected to an external device, and thus, receives fresh air, oxygen, etc. from the external device and transfers the air, oxygen, etc. to the user in the main body 100.

Referring to FIGS. 1 to 3, because the injection portion 500 according to the embodiment of the present disclosure transfers the air, oxygen, etc. into the inner space of the main body 100, the user smoothly breathes during the welding operation, the disinfecting operation, etc., and the operating efficiency may be improved.

Hereinafter, a structure, operating principles, and effects of a facial protection apparatus according to another embodiment of the present disclosure will be described below.

Figure 8:
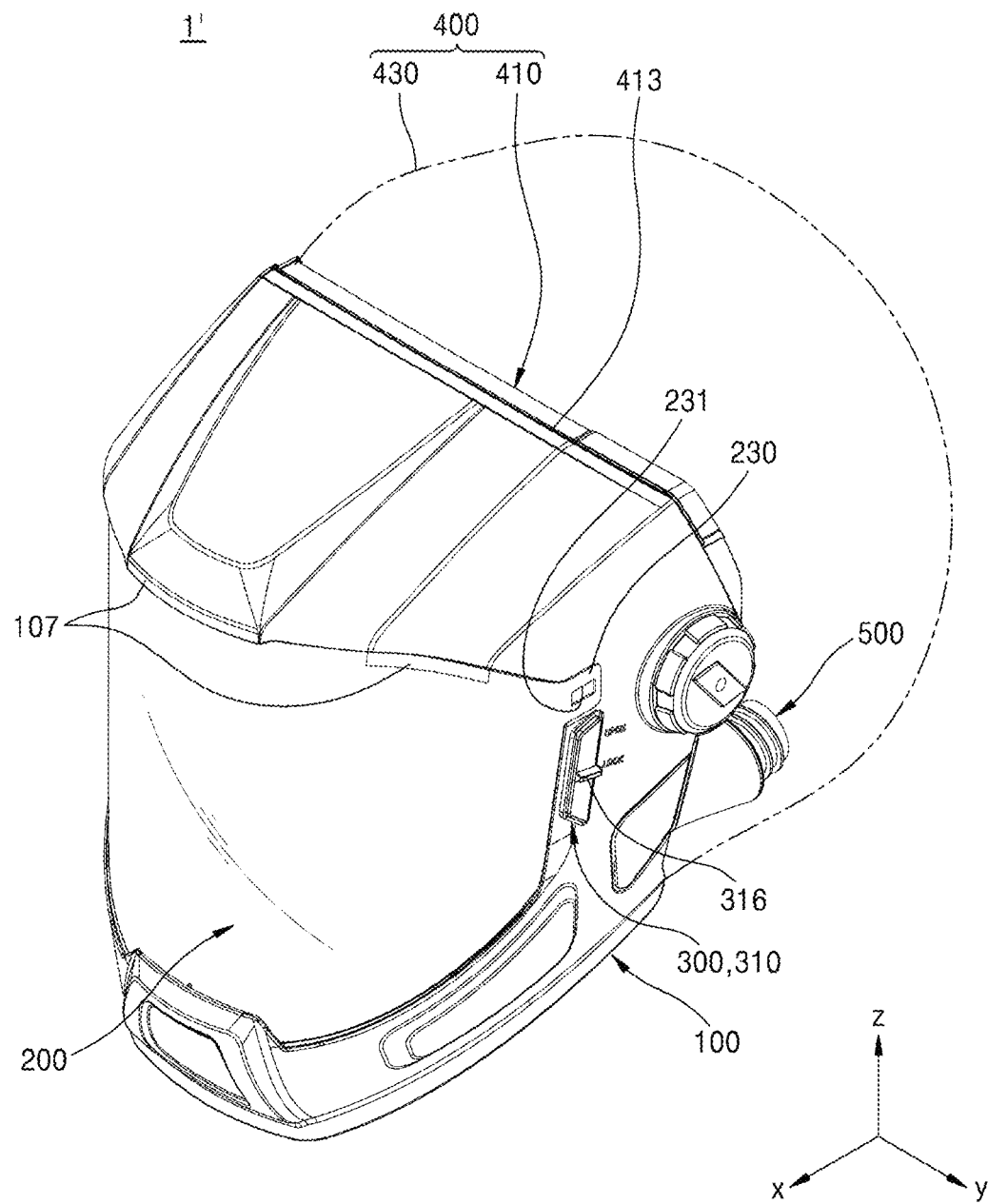
FIG. 8 is a perspective view of a facial protection apparatus according to another embodiment of the present disclosure.

FIG. 8 is a perspective view of a facial protection apparatus 1' according to another embodiment of the present disclosure. Referring to FIG. 8, the facial protection apparatus 1' according to another embodiment of the present disclosure may include the main body 100, the shield portion 200, the opening/closing portion 300, the cover portion 400, and the injection portion 500.

Referring to FIG. 8, the shield portion 200 according to another embodiment of the present disclosure covers the opening area formed in the main body 100, and may be detachably connected to the main body 100.

Referring to FIG. 8, the shield portion 200 according to another embodiment of the present disclosure may have a grip portion 230 protruding from a preset region in an outer end circumference thereof.

Referring to FIG. 8, the grip portion 230 is exposed to outside while the shield portion 200 is inserted in the main body 100, and may be formed as a ring shape including a hole portion 231.

When the grip portion 230 is formed on the shield portion 200 according to another embodiment of the present disclosure, the user may open/close the movement path of the shield portion 200, in particular, the bent portion 211 by moving the opening/closing portion 300 on the main body 100. In addition, when the user grips the grip portion 230 and pulls the grip portion 230 outward, the shield portion 200 may be easily separated and disconnected from the main body 100.

In the facial protection apparatus 1' according to another embodiment of the present disclosure, the structures, the operating principles, and the effects of the main body 100, opening/closing portion 300, the cover portion 400, and the injection portion 500 are the same as those of the facial protection apparatus according to the above embodiment, except for the grip portion 230 formed on the preset region in the outer circumference of the shield portion 200, and thus, detailed descriptions thereof are omitted.

In the facial protection apparatus according to the embodiments of the present disclosure, the main body and the shield portion are not integrally formed with each other, but the shield portion may be inserted in or separated from the main body through a simple operation, and thus is easily replaced.

Also, the opening/closing portion that is movable on the main body opens/closes the movement path of the bent portion that protrudes from the shield portion, in particular, the engagement portion, and thus, separation of the shield portion from the main body during the operation such as the welding operation, the disinfecting operation, etc. may be prevented.

Also, because the shield portion includes a transparent material, the shield portion may block the foreign matters that unexpectedly approach the face of the user, while securing the sight of the user, and thus, risks that the user may have due to the foreign matters may be prevented.

Also, the shield portion may include the light-shielding layer, and thus, when the user performs the welding operation, the intensive light from the welding spot may be blocked and the eyesight of the user may be protected.

Also, the insertion portion is formed in the circumference of the main body, to which the shield portion is connected, to guide the insertion path of the shield portion. In addition, because the shield portion is inserted and fixed into the insertion portion having a certain depth, the introduction of the foreign matters through the connecting region between the shield portion and the main body may be prevented.

Also, because the protrusion portion formed on the cover portion is inserted and seated in the seating portion formed in the main body, the coupling force between the main body and the cover portion may be improved, and the cover portion may be separated from the main body through a simple operation, e.g., pushing the protrusion portion by the user.

While the disclosure has been particularly shown and described with reference to exemplary embodiments thereof, it will be understood by those of ordinary skill in the art that various changes in form and details may be made therein without departing from the spirit and scope as defined by the following claims. Therefore, the scope sought to be protected of the disclosure shall be defined by the appended claims.

In the facial protection apparatus for welding according to the embodiments of the present disclosure, the main body and the shield portion are not integrally formed with each other, but the shield portion may be inserted in or separated from the main body through a simple operation, and thus is easily replaced.

Also, the opening/closing portion that is movable on the main body opens/closes the movement path of the bent portion that protrudes from the shield portion, in particular, the engagement portion, and thus, separation of the shield portion from the main body during the operation such as the welding operation, the disinfecting operation, etc. may be prevented.

Also, because the shield portion includes a transparent material, the shield portion may block the foreign matters that unexpectedly approach the face of the user, while securing the sight of the user, and thus, risks that the user may have due to the foreign matters may be prevented.

Also, the shield portion may include the light-shielding layer, and thus, when the user performs the welding operation, the intensive light from the welding spot may be blocked and the eyesight of the user may be protected.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A facial protection apparatus comprising:
   a main body having an opening area that is opened forward and being wearable by a user;
   a shield portion covering the opening area formed in the main body and detachably connected to the main body; and
   an opening/closing portion installed on the main body and opening/closing an insertion path of the shield portion that is inserted in the main body, wherein the opening/closing portion comprises an opening/closing body that is movable on the main body in a preset linear direction, the opening/closing body includes a passing portion that passes through the main body in a first direction and comes into contact with the main body, at one end of the passing portion, a hook portion is formed to protrude in an extending direction different from the first direction in which the passing portion passes through the main body so as to pass through the main body and is placed on one surface of the main body.

2. The facial protection apparatus of claim 1, wherein the shield portion is formed to have a transparency that varies.

3. The facial protection apparatus of claim 1, wherein the shield portion includes a light-shielding layer.

4. The facial protection apparatus of claim 1, wherein the opening/closing portion comprises a plurality of opening/closing portions that are arranged at opposite sides of the main body on the basis of a center portion of the main body.

5. The facial protection apparatus of claim 1, further comprising a cover portion connected to the main body and configured to surround the head of the user.

6. The facial protection apparatus of claim 5, wherein the cover portion comprises:

a cover frame portion connected to the main body; and a cover body connected to one end portion of the cover frame portion, the end portion being opposite to an end portion of the cover frame portion connected to the main body, and configured to be located on an outside of a back of the head of the user.

* * * * *